United States Patent
Olsson et al.

(10) Patent No.: US 11,739,051 B2
(45) Date of Patent: Aug. 29, 2023

(54) CRYSTALLINE PARTICLES OF BIS-CHOLINE TETRATHIOMOLYBDATE

(71) Applicant: ALEXION PHARMA INTERNATIONAL OPERATIONS UNLIMITED COMPANY, Dublin (IE)

(72) Inventors: Lars Olsson, Uppsala (SE); Viveca T. Oltner, Landskrona (SE)

(73) Assignee: ALEXION PHARMACEUTICALS, INC., Boston, MA (US)

( * ) Notice: Subject to any disclaimer, the term of this patent is extended or adjusted under 35 U.S.C. 154(b) by 402 days.

(21) Appl. No.: 16/968,854

(22) PCT Filed: Feb. 6, 2019

(86) PCT No.: PCT/EP2019/052940
§ 371 (c)(1),
(2) Date: Aug. 10, 2020

(87) PCT Pub. No.: WO2019/154876
PCT Pub. Date: Aug. 15, 2019

(65) Prior Publication Data
US 2021/0094901 A1    Apr. 1, 2021

Related U.S. Application Data

(60) Provisional application No. 62/627,071, filed on Feb. 6, 2018.

(51) Int. Cl.
*A61K 9/14* (2006.01)
*C07C 215/40* (2006.01)
*A61K 9/28* (2006.01)
*A61K 9/48* (2006.01)

(52) U.S. Cl.
CPC .............. *C07C 215/40* (2013.01); *A61K 9/14* (2013.01); *A61K 9/28* (2013.01); *A61K 9/4808* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 6,703,050 B1 | 3/2004 | Brewer et al. | |
| 6,855,340 B2 | 2/2005 | Brewer | |
| 7,189,865 B2 | 3/2007 | Ternansky et al. | |
| 2004/0019043 A1 | 1/2004 | Coucouvanis et al. | |

FOREIGN PATENT DOCUMENTS

WO    2019110619 A1    6/2019

OTHER PUBLICATIONS

International Search Report and Written Opinion for International Application No. PCT/EP2019/052940, dated Apr. 2, 2019.
(Continued)

*Primary Examiner* — Kevin S Orwig
(74) *Attorney, Agent, or Firm* — McDonnell Boehnen Hulbert & Berghoff LLP

(57) ABSTRACT

Novel crystalline particles, methods for manufacture of crystalline particles, and solid unit dosage forms, particularly tablets or capsules, of bis-choline tetrathiomolybdate are provided. In particular, provided herein are crystalline particles that allow for a more stable solid unit dosage form of bis-choline tetrathiomolybdate.

20 Claims, 8 Drawing Sheets

(56) References Cited

OTHER PUBLICATIONS

Degen et al. "The HighScore suite." Powder Diffraction. 2014, 29, p. S13-S18.
Shekunov et al. "Particle Size Analysis in Pharmaceutics: Principles, Methods and Applications." Pharmaceutical Research. 2005, 24, p. 203-227.
Weiss et al. "Bis-chloine tetrathiomolybdate in patients with Wilson's disease: an open-label, multicentre, phase 2 study." Lancet Gastroenterol Hepatol. 2017, 2, p. 869-876.
Matsuoka, Fundamentals and Applications of Crystalline Polymorphism, Popular Edition, 1st Printing, CMC Publishing Co.,Ltd., Oct. 22, 2010, p. 105-117, 181-191.
Stahly, P., Importance of salt selection and crystal polymorph screening for pharmaceuticals, Pharmacy, 2006, vol. 66, No. 6, p. 435-439.
Ashizawa, K. et al., Polymorphic Phenomena of Pharmaceuticals and the Science of Crystallization, Maruzen Planet Co.,Ltd., Sep. 20, 2002, p. 305-317.
Edited by Hirayama, A., Handbook of Organic Compound Crystal Preparation: Principles and Know-How, Maruzen Co., Ltd., Jul. 25, 2008, p. 57-84.

CRYSTALLINE PARTICLES OF BIS-CHOLINE TETRATHIOMOLYBDATE

CROSS-REFERENCE TO RELATED APPLICATIONS

This application is a national stage application under 35 U.S.C. § 371 of International Application No. PCT/EP2019/052940, filed Feb. 6, 2019, which claims priority from U.S. Provisional Patent Application No. 62/627,071, filed Feb. 6, 2018, the disclosures of each incorporated by reference herein in their entirety.

BACKGROUND OF THE DISCLOSURE

Wilson Disease (WD) is an autosomal recessive disorder of impaired copper (Cu) metabolism. Mutations in the ATP7B gene result in deficient production of the Cu-transporter ATPase2, leading to impaired incorporation of Cu into ceruloplasmin, impaired biliary excretion of Cu, increased free and albumin-bound Cu, and Cu accumulation in liver, brain, and other tissues, with resulting organ damage and dysfunction. The prevalence of WD is estimated at 1 in 30,000 people, corresponding to approximately 10,000 individuals in the United States and approximately 15,000 individuals in the European Union.

Bis-choline tetrathiomolybdate (BC-TTM) has been demonstrated to provide Cu control and improvement of hepatic function by once daily dosing in WD patients. Making a successful and pharmaceutically acceptable solid unit dosage form of bis-choline tetrathiomolybdate (BC-TTM), such as one intended for use in treating WD and other conditions, can be challenging because BC-TTM degrades under storage, forced degradation conditions, and, in particular, as a consequence of being tableted. Impurities have been found to form over time in preparations of purified BC-TTM. Therefore, there is an unmet need for a form of BC-TTM that allows for a more stable solid unit dosage form.

SUMMARY OF THE DISCLOSURE

The disclosure provides novel crystalline particles, methods for manufacture of crystalline particles, and solid unit dosage forms, particularly tablets or capsules, of BC-TTM. BC-TTM has the structure:

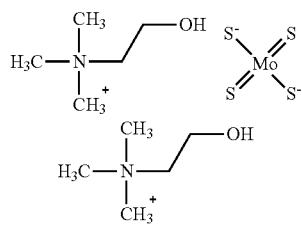

In an embodiment of the disclosed compositions, crystalline particles of bis-choline tetrathiomolybdate have a $50^{th}$ percentile of particle size ($D_{50}$) of at least 30 μm. In other embodiments, the crystalline particles have a $D_{50}$ of at least 40 μm. In other embodiments, the crystalline particles have a $D_{50}$ of between 30 μm and 90 μm. In other embodiments, the crystalline particles have a $D_{50}$ of between 30 μm and 70 μm.

In an embodiment of the disclosed compositions, crystalline particles have a $50^{th}$ percentile of particle size ($D_{50}$) of at least 30 μm, or at least 40 μm, or between 30 μm and 70 μm, and a 90th percentile of particle size ($D_{90}$) of between 75 μm and 550 μm. In other embodiments, the $D_{90}$ is between 400 μm and 550 μm. In other embodiments, the $D_{90}$ is between 75 μm and 135 μm. In other embodiments, the $D_{90}$ is between 75 μm and 100 μm.

The disclosure further provides crystalline particles of BC-TTM having a specific surface area (SSA) less than 0.4 square meter per gram (m²/g) or less than 0.25 m²/g. In an embodiment of the disclosed compositions, less than 40% percent of particles are greater than 100 μm. In other embodiments, 15 and 40 percent of particles are greater than 100 μm. In certain embodiments, a composition of crystalline particles of BC-TTM further comprises impurities. In an embodiment, a composition of crystalline particles of BC-TTM comprise less than 1 percent by mass of the bis-choline salt of $Mo_2S_6O_2^{2-}$. In an embodiment, a composition of crystalline particles of BC-TTM have less than 0.2 percent by mass the bis-choline salt of $Mo_2S_7O^{2-}$. In an embodiment, the percent by mass of the bis-choline salt of $Mo_2S_6O_2^{2-}$ and/or the bis-choline salt of $Mo_2S_7O^{2-}$ is measured after BC-TTM is stored at 40° C. and 75 percent relative humidity for three to six days.

In an embodiment of the disclosed compositions, the crystalline particles have less than 0.5 percent by mass of total impurities. In an embodiment, the total impurities comprise at least one of TM1, TM2, TM3, $Mo_2S_6O_2^{2-}$ and $Mo_2S_7O^{2-}$. In an embodiment, the crystalline particles have a $D_{90}$-to-$D_{50}$ ratio of less than 2.5. In an embodiment, the $D_{50}$ is less than 35 μm. In an embodiment, the $D_{90}$ is less than 75 μm.

In an embodiment of the disclosed compositions, the crystalline particles have a 10th percentile of particle size ($D_{10}$) of less than 15 μm.

The present disclosure further provides methods for manufacture of crystalline particles of bis-choline tetrathiomolybdate (BC-TTM), comprising: (a) providing a solution of BC-TTM; (b) heating the solution of BM-TTM to a first temperature between about 35° C. and 50° C.; (b) gradually adding ethanol or isopropanol to the solution of BC-TTM over a time period of at least one hour; (c) cooling the solution of BC-TTM to a second temperature between about 10° C. and 25° C. to produce solid BC-TTM; (d) filtering the solid BC-TTM; (e) drying the solid BC-TMM at a third temperature between about 20° C. and 30° C. under reduced pressure.

In certain embodiments of the present disclosure, the method comprises washing the solid BC-TTM with ethanol or isopropanol after filtering the solid BC-TTM and prior to drying the solid BC-TTM. In an embodiment, the method comprises de-lumping the crystalline particles, optionally using a conical screen mill.

In other embodiments of the present disclosure, the methods provide BC-TMM wherein the $50^{th}$ percentile of particle size ($D_{50}$) is at least 35 μm. In yet other embodiments, the $D_{50}$ is at least 40 μm. In an embodiment, the $D_{50}$ is between 40 μm and 90 μm. In an embodiment, the solvent comprises water. In an embodiment, the solution of BC-TTM is produced by dissolving BC-TTM that has previously been crystallized one or more times. In an embodiment, the method further comprises polish-filtering the solution of BC-TTM prior to the heating step. In an embodiment, the time period for adding ethanol is at least two hours. In an embodiment, the first temperature is between 40° C. and 45° C. In an embodiment, the second temperature is 15° C. In an embodiment, the third temperature is 25° C. In an embodiment, the method comprises holding the solution at the first temperature for at least one hour. In an embodiment, the method comprises holding the solution at the second temperature for at least one hour. In an embodiment, the method comprises holding the solution at the third temperature for at least one hour.

The disclosure further provides a solid unit dosage form comprising the crystalline particles of bis-choline tetrathiomolybdate as described in any of the embodiments of the disclosed compositions. In an embodiment, the solid unit dosage form comprises a tablet. In an embodiment, a tablet of the disclosure is prepared by direct compression of a mixture of bis-choline tetrathiomolybdate and pharmaceutically acceptable excipients, which is, optionally, coated, or optionally, pre-coated and subsequently coated.

In an embodiment of the present disclosure, the solid unit dosage form is prepared by filling a capsule with a mixture of bis-choline tetrathiomolybdate and pharmaceutically acceptable excipients. In embodiments of the solid unit dosage forms of the present disclosure, the solid unit dosage form is stable for storage and use. In an embodiment, the solid unit dosage form has less than 6 percent by mass of total impurities. In an embodiment, the solid unit dosage form has less than 1.5 percent by mass of total impurities.

Additional aspects and embodiments of the disclosure will be apparent from the detailed description that follows.

DETAILED DESCRIPTION

Figure 1:
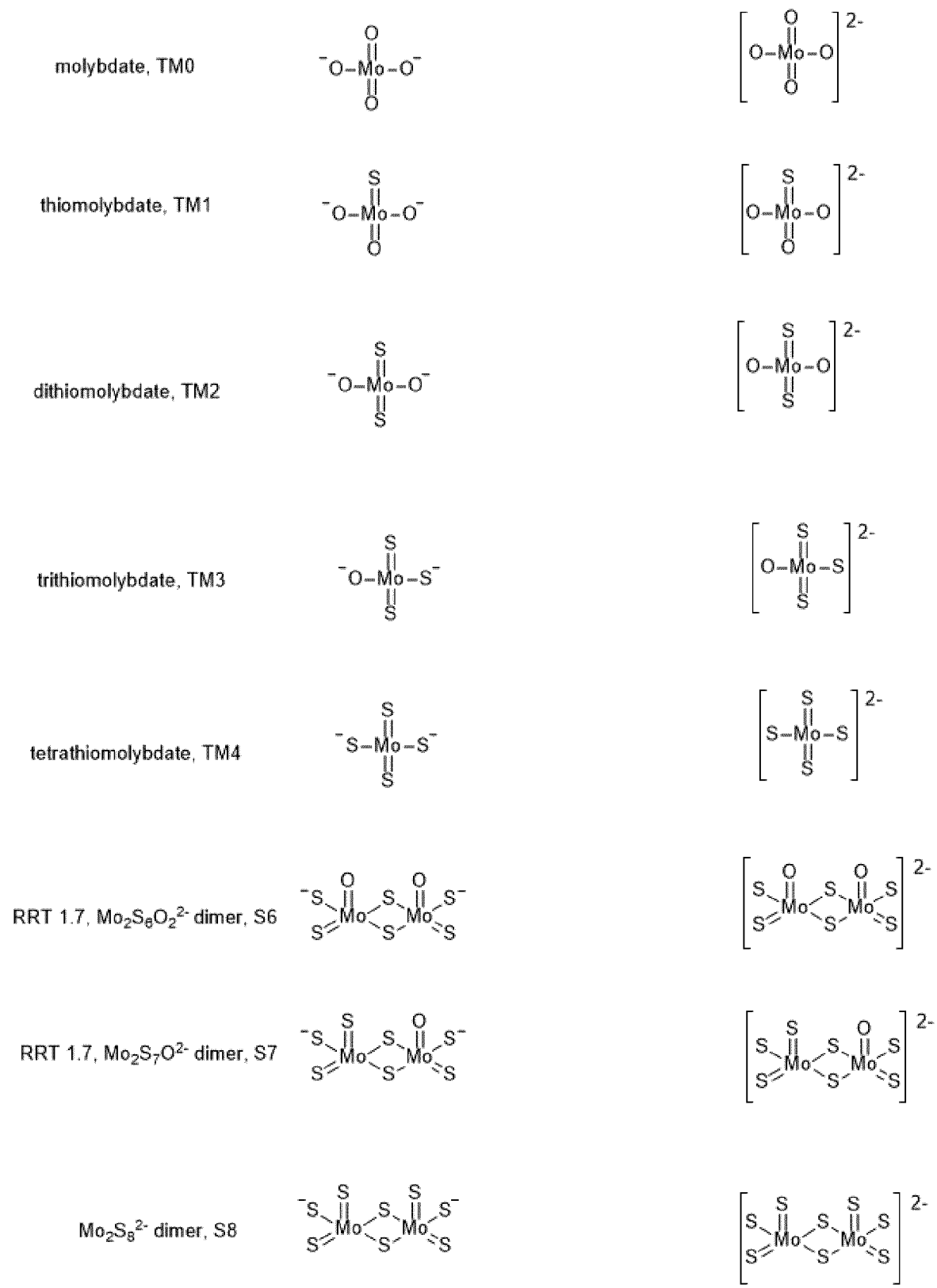
FIG. 1 depicts impurities in compositions comprising bis-choline tetrathiomolybdate. The impurities are present in the form of the bis-choline salt of ions in FIG. 1.
Figure 2:
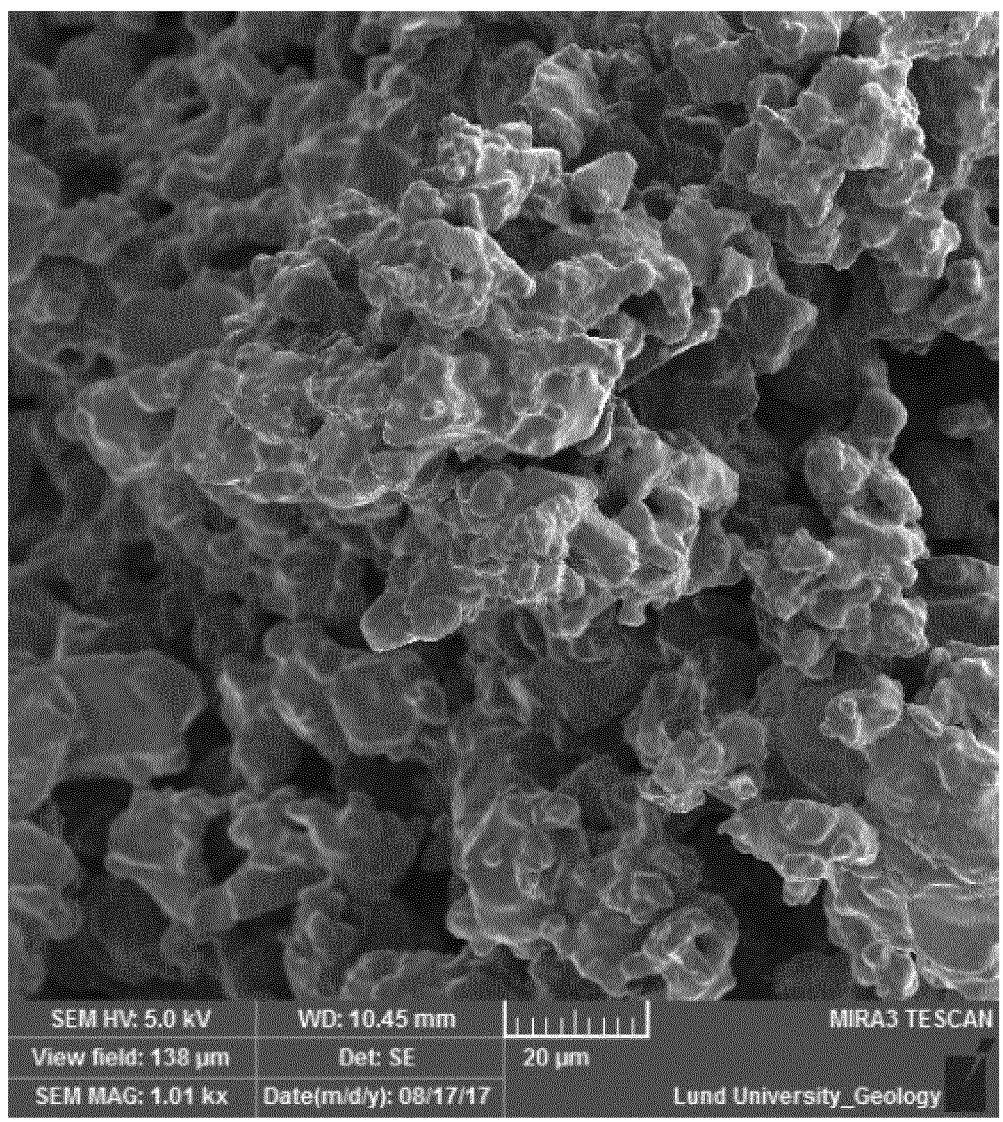
FIG. 2 depicts SEM image of (agglomerated) crystalline particles in batch A-2.
Figure 3:
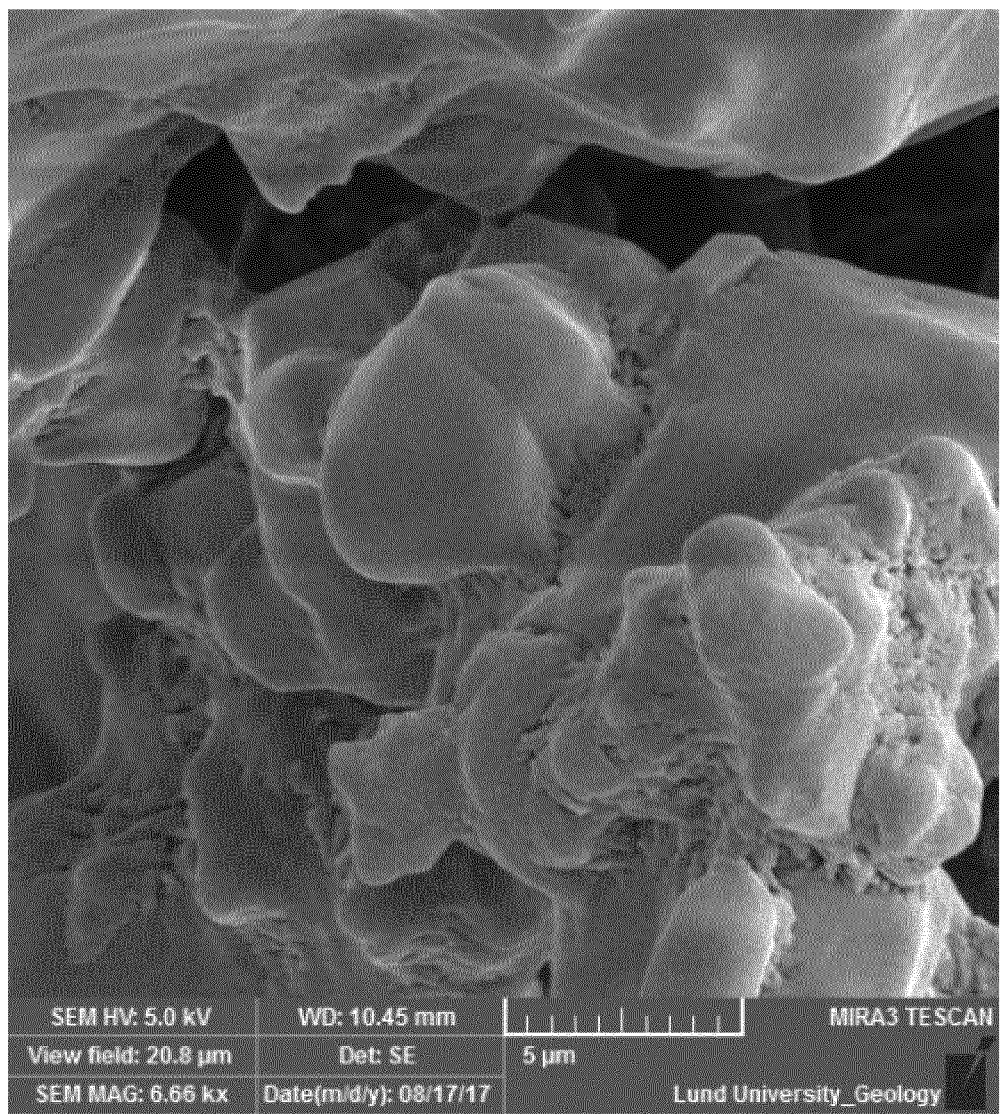
FIG. 3 depicts SEM image of (agglomerated) crystalline particles in batch A-2 at higher magnification.
Figure 4:
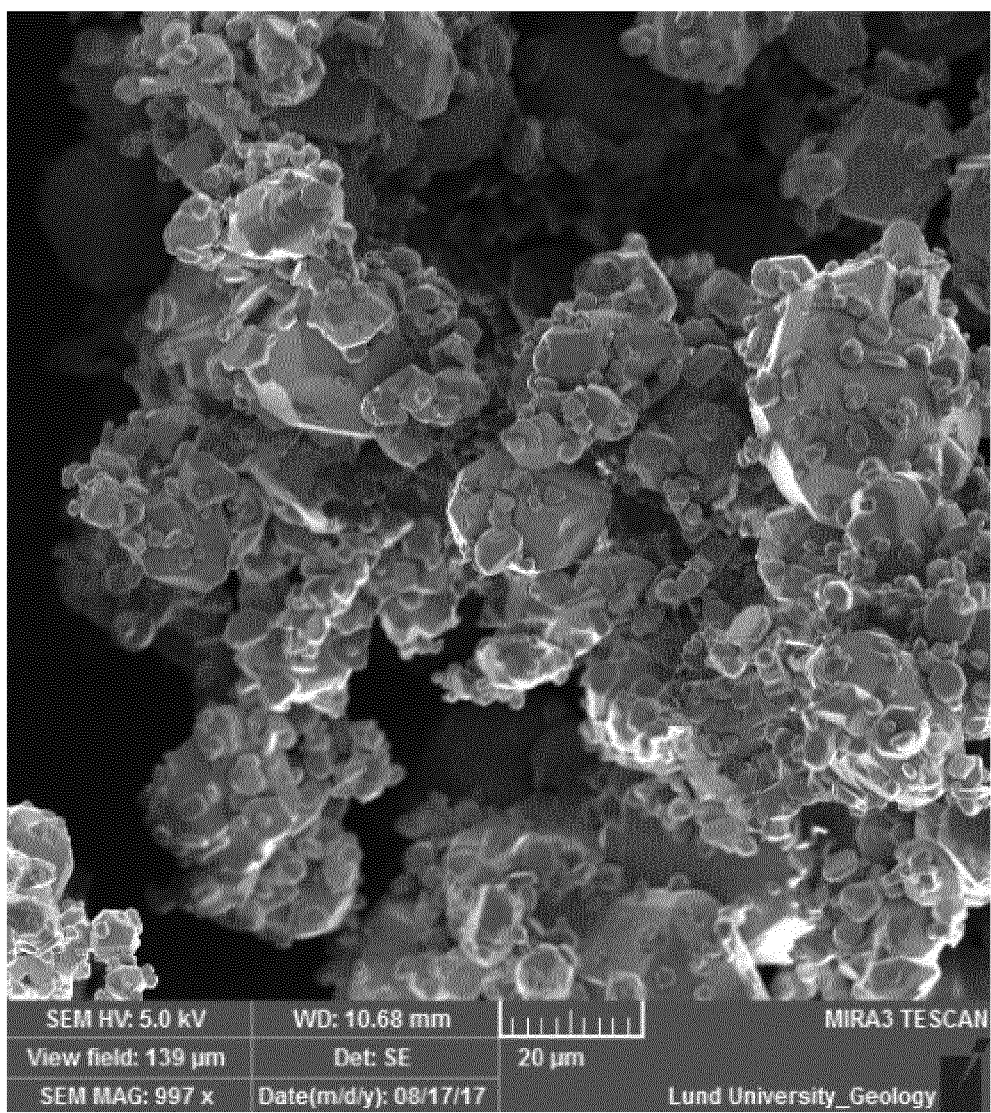
FIG. 4 depicts SEM image of crystalline particles in batch B-3.
Figure 5:
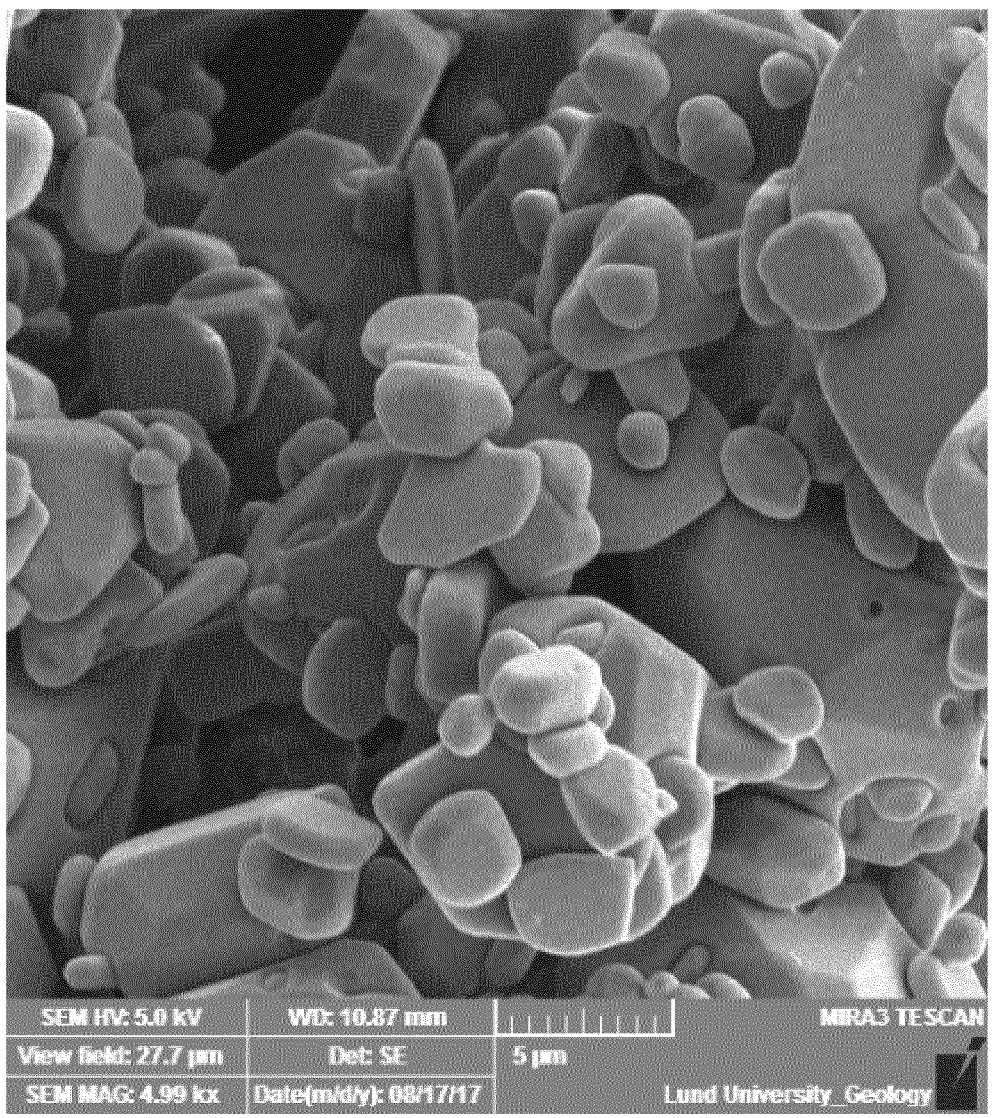
FIG. 5 depicts SEM image of crystalline particles in batch B-3 at higher magnification.
Figure 6:
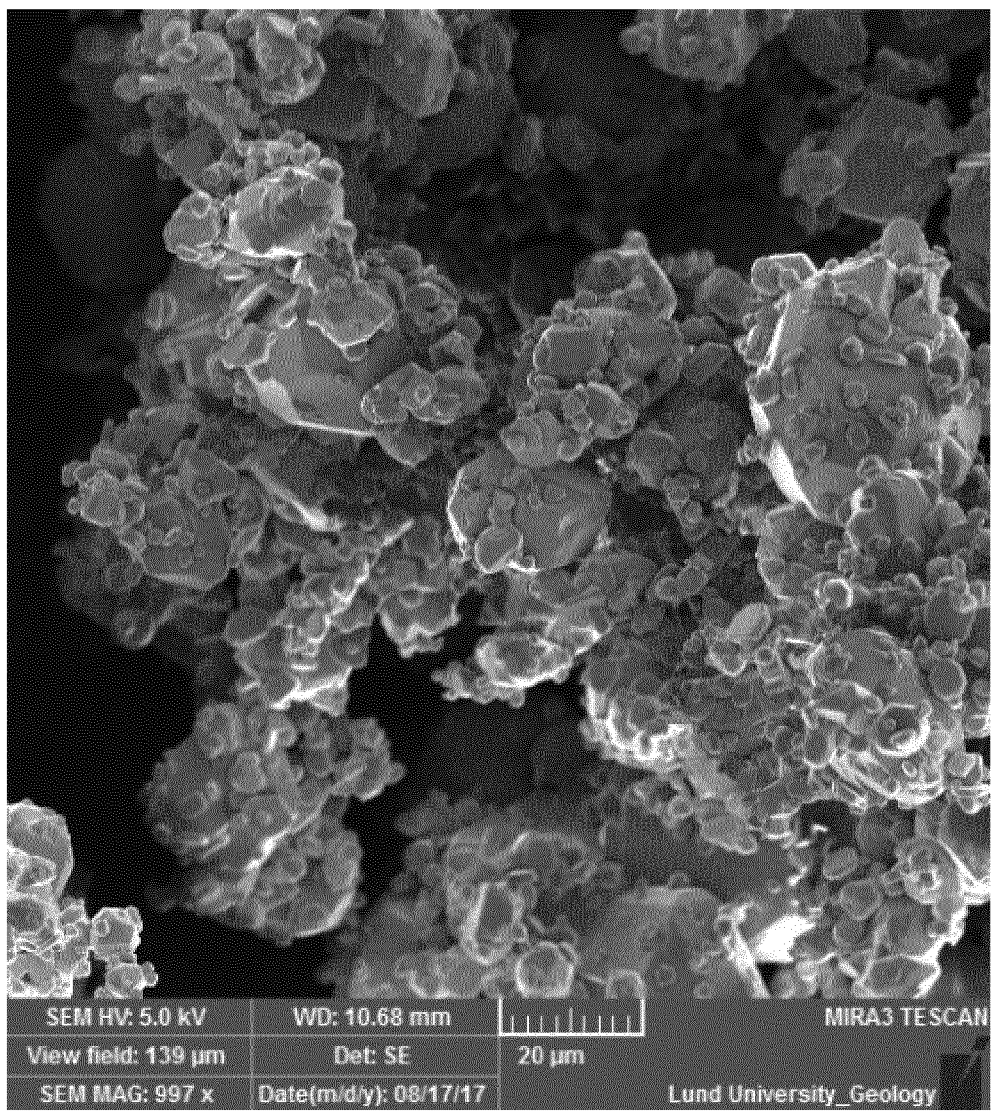
FIG. 6 depicts SEM image of crystalline particles in batch B-1.
Figure 7:
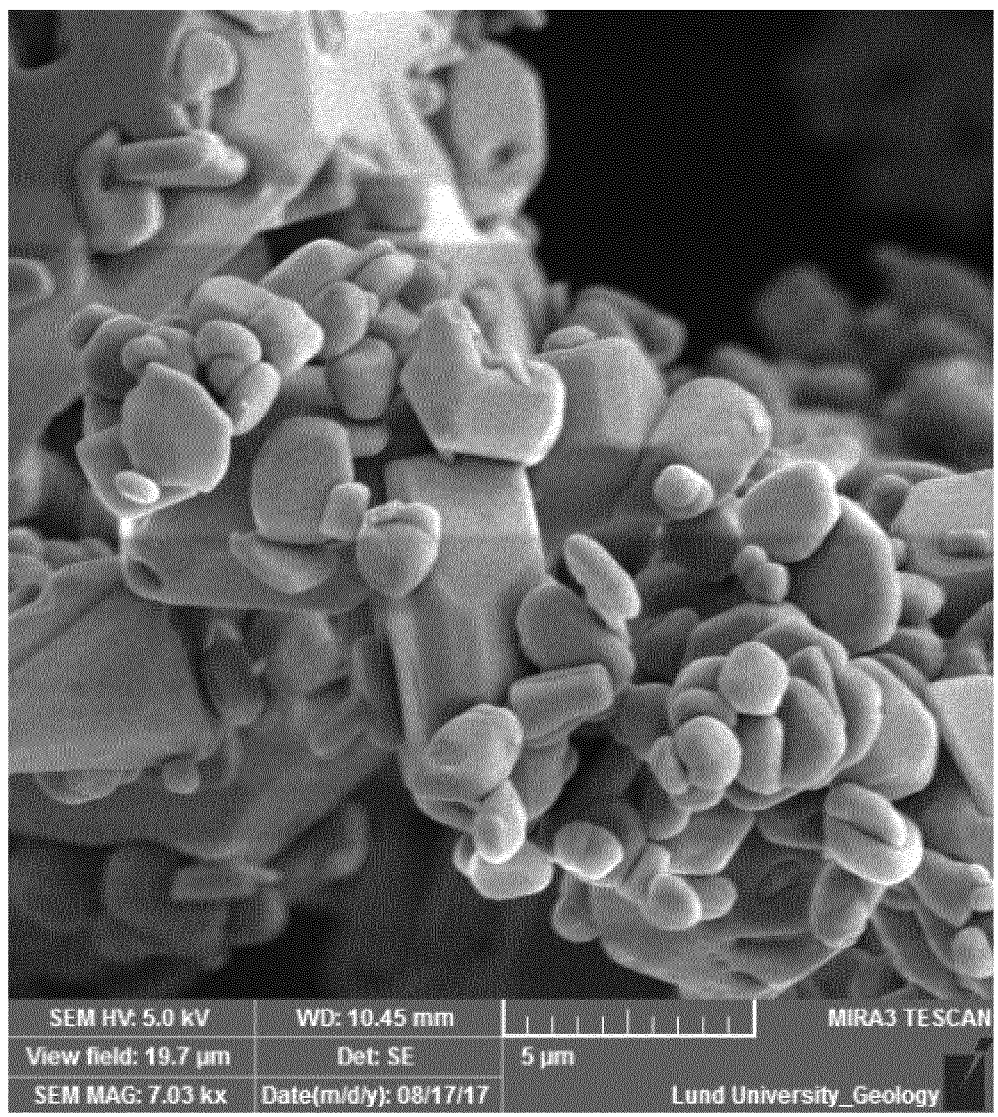
FIG. 7 depicts SEM image of crystalline particles in batch B-1 at higher magnification.

The disclosure provides novel crystalline particles of BC-TTM; methods for manufacture of crystalline particles of BC-TTM; and solid unit dosage forms of BC-TTM including tablets and capsules. The disclosure further provides non-limiting, exemplary methods for manufacturing crystalline particles of BC-TTM. Certain aspects of the present disclosure are based on the surprising discovery that the disclosed methods for manufacturing crystalline particles of BC-TTM result in different particle-size distributions and that certain particle-size distributions correlate with increased stability to chemical degradation of BC-TTM under storage, forced degradation, or tableting.

1.1 Synthesis of Bis-Choline Tetrathiomolybdate

Processes for preparing thiomolybdate derivatives are disclosed in US 2004/0019087 (now U.S. Pat. No. 7,189,865 to "Thiomolybdate analogues and uses thereof"), which is incorporated by reference herein in its entirety. US 2004/0019087 also discloses a method for synthesis of tetrathiomolybdate in the form of a bis-choline salt (BC-TTM) in which choline hydroxide is added to ammonium molybdate in an aqueous solution, and then hydrogen sulfide gas bubbled through the solution at room temperature. It is disclosed that, after purging the solution with nitrogen gas, the solvent (water) was removed repeatedly under reduced pressure to remove ammonia and that the product was redissolved in water and filtered to remove insoluble molybdenum sulfide. US 2004/0019087 discloses that the product was recrystallized from water and isopropanol and washed with ethanol and diethyl ether to provide a 90% yield on a 1.5 g scale. BC-TTM may also be prepared by other methods including methods adapted to large-scale manufacturing of BC-TTM. The disclosure further provides other, non-limiting, methods of synthesizing BC-TTM.

1.2 Analytic Methods

BC-TTM preparations can be characterized and quantitated by methods known in the art. Fourier-transform infrared spectroscopy (FT-IR), nuclear magnetic resonance (NMR), coulometry, X-ray crystallography, and other analytical methods may be used to characterize BC-TTM. The molybdenum content of BC-TTM may be determined by inductively coupled plasma atomic emission spectroscopy (ICP-AES) or other analytical methods. BC-TTM may be analyzed and quantitated by high-performance liquid chromatography (HPLC). For example, liquid chromatography can be performed on the molybdenum ions as ethylenediaminetetraacetic acid (EDTA) complexes using reversed-phase ion-pair liquid chromatography with detection at 242 or 301 nanometers. The disclosure encompasses any form of analytical method known in the art.

1.3 Solid State Characterization of BC-TTM

In some aspects of the disclosure, BC-TTM is characterized by X-ray powder diffraction (XRPD), low-angle light scattering (LALLS), specific surface area determination by the Brunauer-Emmett-Teller (BET) method, or scanning electron microscopy (SEM). The disclosure encompasses any form of solid state characterization known in the art. Detailed methods are provided in the examples that follow.

2.1 Crystalline Particles of Bis-Choline Tetrathiomolybdate

As used herein, "crystalline particles" of BC-TTM means sold particles consisting essentially of BC-TTM in a crystalline state in any polymorphic form. Compositions of "crystalline particles" may contain various amounts of amorphous BC-TTM as well as other constituents and as used herein descriptions of the characteristics of "crystalline particles" refers to characterization of the composition as a whole including amorphous BC-TTM and any impurities present. Crystalline particles of BC-TTM may contain 90% or more, 95% or more, or 99% or more by weight of BC-TTM; and more than 50%, 60%, 70%, 80%, 95%, or 99% of the BC-TTM in such crystalline particles may be in a crystalline form, with the remainder of the BC-TTM in one or more amorphous forms. Crystalline particles may be agglomerated, non-agglomerated, or provided in suspension.

2.2 Methods for Manufacture of Crystalline Particles

Crystalline particles of BC-TTM may be formed by spontaneous formation of crystals from a solution of BC-TTM, or crystallization by be triggered by addition to an aqueous solution of BC-TTM of another solvent. Appropriate solvents for causing BC-TTM to crystalline include ethanol, methanol, and isopropanol, although it will be understood that other solvents may also be appropriate.

Crystalline particles may be made by any of the processes disclosed here and in the examples that follow. In some cases, crystalline particles are made by Process A or Process B or Process C, below, or any of variations thereof. The description that follows is non-limiting and disclosure of particular process steps or variables is not intended to suggest that other options for achieving similar results are not possible in view of the exemplary embodiments provided by this disclosure 2.2.1 Process A In certain embodiments, crystalline particles are obtained by cooling an aqueous solution of tetrathiomolybdate to <5° C., adding choline hydroxide solution at a rate that maintains the solution at <5° C., heating to approximately 30° C., polish filtering and cooling the solution to approximately 20° C., slowly adding ethanol or isopropanol, stirring for not less than 30 minutes, isolating crystalline particles by filtration, washing twice with cool ethanol or isopropanol, and drying the crystalline particles at 25° C. under vacuum. In certain embodiments, a vacuum is applied after heating.

2.2.2 Process B

In yet other embodiments, crystalline particles are obtained by adding ammonium tetrathiomolybdate (1 equiv) to pre-cooled water (15±5° C.) to a reaction vessel, adding choline hydroxide (aq, 45% (w/w), 3.5-6.9 equiv.), gently heating (30±5°), reducing the pressure of the reaction vessel, monitoring until a pH of ≤7.5 is achieved, following by: polish filtering and adjusting the temperature ambient temperature (20±5° C.), adding ethanol or isopropanol over 30 minutes to one hour, cooling the resulting slurry (15±5° C.), isolating the resulting crystalline particles on a filter, washing the residue with ethanol or isopropanol, then drying at 25±5° under reduced pressure, and sieving using a conical screen mill. Prior to drying the crystalline residue can also be re-dissolved in water, recrystallized by the addition of ethanol or isopropanol, filtered, and washed again by ethanol or isopropanol.

2.2.3 Process C

In still further embodiments, crystalline particles are obtained by adding ammonium tetrathiomolybdate (1 equiv) to pre-cooled water (15±5° C.) in a reaction vessel, adding choline hydroxide (aq, 45% (w/w), 3.5-6.9 equiv.) to the vessel and heating (30±5°) the resulting mixture while reducing the pressure. Reaction progress can be monitored by measuring evolving ammonia in the reaction vessel out stream every hour using moist pH-sticks. The pH decreases as the reaction progresses, and a pH of ≤7.5 indicates that the reaction is complete. Water loss during the reaction is measured and compensated for by the addition of water at the end of reaction after the pressure is normalized. The final reaction mixture is then polish filtered and the resulting solution adjusted to a temperature of 35 to 50° C. Ethanol or isopropanol is charged to crystallize the crude product and the slurry is then cooled (15±5° C.) and the mixture was left to mature. The crystalline particles are isolated on a filter and washed twice with ethanol or isopropanol. The isolated moist crystalline particles are then re-dissolved in water and the resulting solution is polish filtered and adjusted to of 35 to 50° C. Ethanol is charged over at least 2 h to crystallize the product and the slurry is then cooled (15±5° C.) and the mixture is left to mature. The crystalline particles are isolated by filtration, and washed twice with ethanol or isopropanol. The crystalline particles can then be dried, optionally under pressure, to a constant weight and the resulting dry solids are de-lumped. De-lumping may be performed by any method suitable in the art, such as, but not limited to, sieving through a conical screen mill In some cases, crystalline particles of BC-TTM are made by heating a solution of BM-TTM to between about 35° C. and 50° C., gradually adding ethanol or isopropanol to the solution of BC-TTM over at least one hour, cooling the solution of BC-TTM to about 10° C. and 25° C. to produce solid BC-TTM, filtering the solid BC-TTM, and drying the solid BC-TMM at between about 20° C. and 30° C. under reduced pressure. The resulting solid may then be de-lumped as described above.

The heating step can be can be performed at between 30 and 40° C., between 40 and 50° C., between 30 and 35° C., between 35 and 40° C., between 40 and 45° C., or between 45 and 50° C. In some cases, the heating step may be performed at temperatures slightly below 35 degrees C. or slightly above 50° C. The drying step can be performed at between 20 and 30° C., between 20 and 25° C., or between 25 and 30° C. In some case, the heating step is performed at between 40° C. and 45° C., the cooling step is performed at 15° C., and the drying step is performed at 25° C.

Gradual addition of ethanol or isopropanol may be performed with a pure ethanol solution or an ethanol solution contained up to 5%, 10%, or 15% water. It may be performed with pure isopropanol or an isopropanol solution contained up to 5%, 10%, or 15% water. A mixture of ethanol and isopropanol, which may include some water, can also be used for this step of the manufacturing process.

2.3 Non-Limiting Description of Characteristics of Crystalline Particles

In some cases, crystalline particles of BC-TTM may have a $10^{th}$ percentile of particle size ($D_{10}$) of less than 10, 15, 20, 25, or 30 μm.

In some cases, crystalline particles of BC-TTM may have a $50^{th}$ percentile of particle size ($D_{50}$) of at least 25, 30, 35, 40, 45, 50, 55 60, 65, 70, 75, 80, 85, or 90 μm, or any number between those values, such as at least 30, 31, 32, 33, 34, 35, 36, 37, 38, 49, or 40 μm. In some cases, the $D_{50}$ may be between 30 and 90 μm, between 30 and 70 μm, or between 30 and 60 μm. In some cases, the $D_{50}$ may be between 30 and 35, between 32 and 37, between 35 and 40, between 37 and 42, between 40 and 45, between 42 and 47, between 45 and 50, between 47 and 52, between 47 and 55, between 50 and 55, between 50 and 60, between 50 and 65, or between 50 and 70 μm.

In some cases, crystalline particles of BC-TTM may have a $90^{th}$ percentile of particle size ($D_{90}$) of at least 60, 70, 80, 90, or 100 μm. In some cases, the $D_{90}$ is at least 400, 420, 440, 460, 480, or 500 μm. In some cases, the $D_{90}$ is at least 75, 80, 85, 90, 95, or 100 μm. In some cases, the $D_{90}$ may be between 60 and 550 μm, or between 400 and 550 μm, or between 75 and 135 μm, or between 75 and 100. In other cases, the $D_{90}$ may be between 70 and 80, 70 and 75, 70 and 80, 70 and 90, 75 and 80, 75 and 85, 75 and 90, 75 and 95, 80 and 85, 80 and 90, 80 and 95, 80 and 100, 85 and 90, 85 and 95, 85 and 100, 90 and 95, or 90 and 100 μm.

In certain embodiments, the BC-TTM particles may have $D_{50}$ and $D_{90}$ particle sizes as recited above. In some cases, it is advantageous to make crystalline particles of BC-TTM in which the $D_{50}$ is between 30 and 90 μm, between 35 and 80 μm, or between 40 and 60 μm; and the $D_{90}$ is between 75 and 120 μm, 80 and 110 μm, or 85 and 105 μm.

It may also be advantageous to make crystalline particles of BC-TTM in which the $D_{90}$-to-$D_{50}$ ratio is within certain ranges. As used here, the $D_{90}$-to-$D_{50}$ ratio refers to the ratio of the D90 value to the $D_{50}$ value. As a non-limiting example, if the $D_{90}$ was 75 μm and the $D_{50}$ was 50 μm, the $D_{90}$-to-$D_{50}$ ratio would be 1.5 (75:50). In some cases, the $D_{90}$-to-$D_{50}$ ratio is between 1.3 and 3, or any ratio between those values. In some cases, the $D_{90}$-to-$D_{50}$ ratio is 1.3, 1.4, 1.5, 1.6, 1.7, 1.8, 1.9, 2.0, 2.1, 2.2, 2.3, 2.4, 2.5, 2.6, 2.7, 2.8, 2.9, or 3.

In some cases, the specific surface area (SSA) will be measured and control such that the SSA is less than 0.25 square meter per gram (m$^2$/g), or less than 0.4 m$^2$/g, or less than 0.7 m$^2$/g. In some cases, the SSA is less than 0.1, 0.15, 0.2, 0.25, 0.3, 0.35, or 0.4 m$^2$/g. In some cases, the SSA is less 0.21, 0.22, 0.23, 0.24, 0.25, 0.26, 0.27, 0.28, 0.29, or 0.3 m$^2$/g.

In some cases, the percentage of particles more than 100 μm in size will be less than 20%, 30%, 40%, or 50%. In some cases, the percentage of particles more than 100 μm in size will be less than 35%, 36%, 37%, 38%, 39%, 40%, 41%, 42%, 43%, 44%, or 45%. In some cases, the percentage of particles less than 2 μm in size will be less than 1%, 2%, 3%, 4%, 5%, 6%, or 7%.

In any of the compositions of the present disclosure, the compositions of crystalline particles may comprise total impurities (defined as the total of the percentage by mass of bis-choline salts of TM1, TM2, TM3, $Mo_2S_6O_2^{2-}$ and $Mo_2S_7O^{2-}$, shown in FIG. 1) of less than 10%, 9%, 8%, 7%, 6%, 5%, 4%, 3%, 2%, 1%, or 0.5%, particularly less than or equal to 6%. In some cases, percentage by mass of bis-choline salts of $Mo_2S_6O_2^{2-}$ is less than 2%, 1.75%, 1.5%, 1.25%, 1%, 1.75%, 0.5%, or 0.25%. In some cases, percentage by mass of $Mo_2S_7O^{2-}$ is less than 2%, 1.75%, 1.5%, 1.25%, 1%, 1.75%, 0.5%, or 0.25%. Such impurities may be present, and measured, shortly after crystallization or tableting, or after storage of the compositions or tablet at below 0° C., below 4° C., ambient temperature, 30° C., 35° C., 40° C., or at a higher temperature. The length of storage before measurement may be as short as 1 day or as long as three years. Impurities can also be measured in either the crystalline composition or tablets after said compositions or tablets are stored under accelerated conditions, such as storage at 40° C. and 75 percent relative humidity for three to six days.

2.4 Solid Unit Dosage Forms of Bis-Choline Tetrathiomolybdate

Crystalline particles of BC-TTM may be formulated in various solid dosage form, as described in *Remington: The Science and Practice of Pharmacy*, 21$^{st}$ ed. (2006). In certain embodiments, crystalline BC-TTM is made into a tablet or a capsule. In certain embodiments, the particles can be reduced in size in the presence of one or more excipients or stabilizers, such as but not limited to a surfactants, polymers, electrolytes, and non-electrolytes, and mixtures thereof. Alternatively, the particles can be contacted with one or more excipients or stabilizers after they are reduced in size. The particles of this disclosure can be prepared in a method comprising the steps of dispersing a drug substance in a liquid dispersion medium and applying mechanical means in the presence of grinding media to reduce the particle size of the drug substance to the desired size. Tablets may be coated; or may be pre-coated and then coated with an additional coat. The coating may be an enteric coating or a controlled release coating. In certain embodiments, the solid unit dosage form is a capsule comprising BC-TTM, and optionally, suitable excipients. The capsule may be a hard-shell capsule, such as, but not limited to, as a gelatin or hydroxypropyl methylcellulose (HPMC).

2.5 Methods of Treatment

The present disclosure also contemplates treating Wilson Disease in a patient in need thereof by administering crystalline particles of BC-TTM or solid unit dosage form(s) of such particles. In particular, the disclosure relates to administering between 15 and 90 mg per day of BC-TTM or 15 mg every other day of BC-TTM in the form of crystalline particles with the particle size, stability, and impurity levels disclosed herein. Exemplary methods of treatment for Wilson's disease are provided, for example, in PCT/EP2018/083551 and its priority documents, which are incorporated herein in their entirety. Further methods of using tetrathiomolybdate compounds for cancer, aberrant vascularization, and other conditions are provided by U.S. Pat. Nos. 6,703,050 and 6,855,340; and by U.S. Patent Publication No. US2004/0019043. The present disclosure contemplates the treatment of cancer and any of various Cu accumulation disorders with any of the compositions or solid unit dosage form(s) of the present disclosure.

3. Definitions

As used herein, the term "scale" refers to the approximate yield in kilograms (kg) of a synthetic process for BC-TTM. "Batch" refers to the BC-TTM material, including any impurities, resulting from a synthetic process for BC-TTM.

As used herein, the term "Dx(10)/μm" refers to the 10th percentile of particle size ($D_{10}$) measured in micrometers (μm). As used herein, the terms "Dx(50)/μm" or "median particle size" refer to the 50$^{th}$ percentile particle size ($D_{50}$). As used herein, the term "Dx(90)/μm" refers to the 90th percentile of particle size ($D_{90}$).

As used herein, the term "<2 μm (%)" refers to the percentage (%) of particles that are less than 2 μm. As used herein, the term ">100 μm (%)" refers to the percentage (%) of particles that are greater than 100 μm. As used herein, the percentage of particles refers to the percentage based on the population, or number, of particles.

As used herein, the ten "SSA (m$^2$/g)" refers to specific surface area (SSA) measured in square meters (m$^2$) per gram (g). SSA was measured by BET according to the method described in Example 4. Other methods for BET or other methods for analytical determination of SSA may be used, and will give comparable results.

As used herein, the term "WTX101" refers to bis-choline tetrathiomolybdate, abbreviated BC-TTM.

In the present disclosure, any concentration range, percentage range, ratio range, or integer range is to be understood to include the value of any integer within the recited range and, when appropriate, fractions thereof (such as one tenth and one hundredth of an integer), unless otherwise indicated.

In the present disclosure, the term "about," when immediately preceding a number or numeral, means that the number or numeral ranges plus or minus 10%.

In the present disclosure, the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives.

As used herein, the terms "include" and "comprise" are used synonymously.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

The section headings used herein are for organizational purposes only and are not to be construed as limiting the subject matter described.

The disclosure is further described in the following Examples, which do not limit the scope of the invention as described and claimed in the numbered claims.

EXAMPLES

Example 1: Synthesis of Batches A-1 and A-2

Starting material ammonium tetrathiomolybdate (ATTM) was dispersed in water, and the resulting solution was cooled to <5° C. A choline hydroxide solution was then charged at a rate which maintained the solution at <5° C. After completion of the choline hydroxide charge, a solution was obtained that was subsequently heated to approximately 30° C. A vacuum was applied releasing and removing ammonia from the reaction mixture. The reaction was monitored by checking the pH of the exhaust vapors with moist pH-sticks.

After the reaction was completed, the solution was polish filtered and cooled to approximately 20° C. Ethanol was slowly added to avoid a temperature increase and crystallization of BC-TTM was initiated upon the ethanol addition. After completion of the ethanol addition, the solution was stirred for at least 30 minutes. The crude crystalline particles were isolated by filtration and washed twice with cool ethanol. The crude crystalline particles were dried at 25° C. under vacuum. The typical yield was approximately 80-90% for a 3-12 kg batch.

The synthesis process was performed an additional time according to the methods described. The two batches of crystalline particles that resulted were assigned identifiers A-1 and A-2, respectively, which are used to identify these batches throughout the present disclosure.

Example 2: Synthesis of Batches B-1, B-2, B-3, B-4

Ammonium tetrathiomolybdate (1 equiv) was added to pre-cooled water (15±5° C.) in a reaction vessel. Choline hydroxide (aq, 45% (w/w), 3.5-6.9 equiv.) was then added, and the resulting mixture was gently heated (30±5°) and the pressure in the reaction vessel was reduced using a vacuum pump. Progress of the reaction was monitored by measuring evolving ammonia in the reaction vessel out-stream once every hour using moist pH-sticks. The pH decreased as the reaction progressed. A pH of ≤7.5 indicated that the reaction was complete.

During the reaction, a portion of the water evaporated due to the reduced pressure. This water loss was measured and compensated for by the addition of water at the end of reaction after the pressure was normalized. The final reaction mixture was then polish filtered and the resulting solution adjusted to ambient temperature (20±5° C.). Ethanol was charged over 30 min-1 h to crystallize the crude product and the slurry was then cooled (15±5° C.) and the mixture was left to mature. The crude crystalline particles were isolated on a filter and washed twice with ethanol.

The isolated moist crude crystalline particles were then re-dissolved in water and the resulting solution was polish filtered and adjusted to ambient temperature (20±5° C.). Ethanol was added over from 30 minutes to one hour to crystallize the product, and the slurry was then cooled (15±5° C.) and the mixture was left to mature. The crystalline particles were isolated on a filter, and washed twice with ethanol.

The resulting crystalline particles were discharged from the filter, placed on plastic foil covered metal plates and dried at 25±5° under reduced pressure to constant weight in a drying cabinet. The dry solids were then sieved using a conical screen mill before being packed in plastic bags. The plastic bags were sealed with cable ties, and each bag placed inside a larger aluminum bag together with a drying agent bag. The aluminum bags are heat sealed and stored at <−18° C.

The synthesis process was performed an additional three times according to the methods described. The four batches of crystalline particles that resulted were assigned identifiers B-1, B-2, B-3, and B-4, respectively, which are used to identify these batches throughout the present disclosure.

Example 3: Synthesis of Batch C-1

Ammonium tetrathiomolybdate (1 equiv) was added to pre-cooled water (15±5° C.) in a reaction vessel. Choline hydroxide (aq, 45% (w/w), 3.5-6.9 equiv.) was then added and the resulting mixture is gently heated (30±5°) and the pressure in the reaction vessel was reduced using a vacuum pump. Progress of the reaction was monitored by measuring evolving ammonia in the reaction vessel out stream every hour using moist pH-sticks. The pH decreased as the reaction progresses. A pH of ≤7.5 indicated that the reaction was complete.

During the reaction, a portion of the water evaporated due to the reduced pressure. This water loss was measured and compensated for by the addition of water at the end of reaction after the pressure was normalized. The final reaction mixture was then polish filtered and the resulting solution adjusted to a temperature of 45±3° C. Ethanol was charged to crystallize the crude product and the slurry was then cooled (15±5° C.) and the mixture was left to mature. The crystalline particles were was isolated on a filter and washed twice with ethanol.

The isolated moist crystalline particles were then re-dissolved in water and the resulting solution was polish filtered and adjusted to of 45±3° C. Ethanol was charged over 2.5 hours to crystallize the product and the slurry was then cooled (15±5° C.) and the mixture was left to mature. The crystalline particles were isolated on a filter, and washed twice with ethanol.

The crystalline particles were discharged from the filter, placed on plastic foil covered metal plates and dried at 25±5° under reduced pressure to constant weight in a drying cabinet. The dry solids were then sieved using a conical screen mill before being packed in plastic bags. The plastic bags were sealed with cable ties, and each bag placed inside a larger aluminum bag together with a drying agent bag. The aluminum bags were heat sealed and stored at <−18° C.

The batch of crystalline particles that resulted was assigned identifier C-1, which is used to identify this batch throughout the present disclosure. Additional batches were made by this process and assigned identifiers C-2 and C-3.

Example 5: Crystallinity

Crystallinity was analyzed by X-ray powder diffraction (XRPD) using a Cu-anode (45 kV/40 mA), a Kα-1 monochromator and silicon-based position-sensitive 1D detector (Malvern Panalytical, X'Celerator™). The 2-theta range was 2-35° using a scan speed of 0.02°/s and a step size of 0.017°. Slow spinning sample holders were used. Samples taken from each of the batches were analyzed sequentially. Each sample was smeared out using a Teflon bar, producing a flat powdered surface on zero background wafers of silicon (Si). The measurements were performed using a programmable incident divergence slit.

The crystallinity was evaluated using Panalytical HighScore Plus™ software (The HighScore suite; T. Degen, M. Sadki, E. Bron, U. König, G. Nénert; *Powder Diffraction*, Volume 29, Supplement S2, December 2014, pp S13-S18). This method is based on the following steps: 1) Calculation of the net area of the signals from the crystalline part of the sample. This area is defined as "AREAcryst." 2) Calculation of the net total area, that is, area from the amorphous "humps" plus the net peak area from step 1. This area is defined as "AREAtotal." In the calculation of above areas, an automatic correction of the background is made by using data collected for an empty sample holder. 3) The percent crystallinity of the sample is calculated as: (AREAcryst/AREAtotal)*100.

XRPD crystallinity results for each batch are reported Table 1.

TABLE 1

| Batch Number | Estimated Crystallinity (%) |
| --- | --- |
| 1. B-4 | 93 |
| 2. B-1 | 92 |
| 3. B-2 | 93 |
| 4. B-3 | 95 |
| 5. C-1 | 93 |
| 6. A-2 | 86 |

Example 4: Particle Size Distribution and Specific Surface Area

Particle size distribution (PSD) was analyzed by LALLS on a commercial laser particle size analyzer (Malvern Instruments Ltd. Mastersizer 3000™) instrument, equipped with a 300 mm reverse Fourier lens with a small volume automated liquid sample dispersion unit (Malvern, Hydro MV™). The sample dispersion medium was paraffin oil. Samples taken from each of the batches were analyzed sequentially. Each sample was introduced directly into the small volume sample dispersion unit to study the disaggregation under influence of stirring only. Thereafter sonication was applied at low power (20%) in 60 seconds. This was repeated until a stable reading was obtained.

The PSD measurements were done using the following settings: background measurement time, 20 seconds(s); sample measurement time, 20 s; dispersant refractive index, 1.45; particle refractive index, N/A (Fraunhofer), absorption, N/A (Fraunhofer); stirrer speed, 2500 rpm; analysis model: general purpose.

Specific Surface Area (SSA) was analyzed by BET on a surface area analyzer (Gemini 2375™ from Micromeritics Instrument Corp.). Samples taken from each of the batches were analyzed sequentially. Each sample was filled into a glass tube and "degassed" at 30° C. for 1 h under continuous $N_2$ (g) flow in order to remove all loosely bound molecules on the external surface and from potential channels in the material. Simultaneously, the saturation pressure for the liquid nitrogen used was determined. After weighing the degassed samples, the degassed samples were inserted into the measuring position at −196° C. (boiling point for liquid nitrogen), evacuated and then exposed to a range of partial pressures basically covering the whole range from almost zero to close to 1 under adsorption mode. The lower pressures were used for SSA determination. Higher pressures were used for potential micro pore determination. In order to ascribe the right amount of nitrogen to the substances, the free volume in the tubes was measured with helium gas prior to nitrogen adsorption. The appropriate thickness values for the adsorbed layer (above the point where no absorption took place in micro pores anymore) was determined from a t-plot and subsequently used to correct the calculation by separating the adsorbed nitrogen molecules into either absorbed into potential pore like structures (the "micro pore volume") or adsorbed onto actual external surface.

PSD and SSA measurements for each batch are reported in Table 2.

TABLE 2

| Batch | Scale | Dx (10)/μm | Dx (50)/μm | Dx (90)/μm | <2 μm (%) | >100 μm (%) | SSA ($m^2/g$) |
| --- | --- | --- | --- | --- | --- | --- | --- |
| A-1 | 4 kg | 10.3 | 59.4 | 503 | 2 | 42.1 | 0.52 |
| A-2 | 12 kg | 25.5 | 86.6 | 442.0 | 0.0 | 46.8 | 0.26 |
| B-1 | 10 kg | 5.8 | 21.6 | 60.8 | 4.0 | 0.9 | 0.60 |
| B-2 | 10 kg | 5.4 | 20.5 | 59.7 | 4.3 | 0.1 | 0.65 |
| B-3 | 10 kg | 10.5 | 30.0 | 54.9 | 2.6 | 0.0 | 0.38 |
| B-4 | 10 kg | 3.6 | 12.7 | 47.6 | 6.6 | 0.0 | 1.16 |
| C-1 | 10 kg | 26.0 | 51.3 | 90.9 | 1.21 | 6.11 | 0.13 |
| C-2 | 10 kg | 25.7 | 49.9 | 87.7 | 0.8 | 5.1 | 0.14 |
| C-3 | 10 kg | 25.7 | 52.9 | 97.7 | 1.0 | 9.2 | 0.12 |

Example 5: Microscopy Images

Microscopic images were taken by scanning electron microscope (SEM) using a sputter coater (Cressington Scientific Instruments, Cressington 208A™) and an electron microscope (Tescan® Mira 3™). The sputter parameters were 40 mA and 15 nm. The imaging mode was backscatter and secondary electron imaging. The sample condition was 5 kV, WD: 10 mm, X27-X7000. Samples taken from batches were analyzed sequentially. Each sample was spread onto adhesive carbon tape on a SEM sample holder stub. The sample was then coated with a 15 nm layer of platinum/palladium (Pt/Pd) in a sputter coating chamber producing a conducting surface. The sample was investigated with SEM at different levels of magnification to give both an overview of the morphology of particles and agglomerates and a detailed view of the surface structure of primary particles.

Representative SEM images are shown in FIGS. 2-7.

Example 6: Tableting

Tablets were prepared from crystalline particles. Batches B-1 and C-1 were tableted, sequentially, as follows. Crystalline particles from each batch were individually compounded with excipients in a dry powder blend followed by dry granulation. The granulate was tableted by direct compression, followed by coating of the tablet cores. Coating consisted of a pre-coat followed by an enteric coat. The tablets were packaged in thermoform blister packages.

Example 7: Purity Analysis

Purity was analyzed by reverse-phase high-performance liquid chromatography (HLPC) using Agilent® 1100 series HPLC system and a reversed-phase column (Aquasil C18, 4.6×250 mm, 5 μm) at 25°, with the absorbance detector set to 242 or 301 nm. Disodium molybdate dihydrate or bischoline tetrathiomolybdate were used as a reference standards. The amount of BC-TTM and impurities in the sample solution was determined by the regression line and the area of the standard peaks in the sample chromatogram. The identities of the observed chromatogram peaks is disclosed in Table 3. Chemical structures of the impurities are disclosed in FIG. 1.

TABLE 3

| Compound | Approximate Retention Time (minutes) | RRT* | 1/RRF |
|---|---|---|---|
| Bischoline Thiomolybdate (TM1) | 4.7 | 0.48 | 1.00** |
| Bischoline Dithiomolybdate (TM2) | 5.9 | 0.61 | 1.00 |
| Bischoline Trithiomolybdate (TM3) | 7.7 | 0.78 | 0.67 |
| Tetrathiomolybdate (BC-TTM) | 9.9 | 1.00 | — |
| Impurity RRT 1.7 (Dimer $Mo_2O_2S_6^{2-}$) | 16.5 | 1.7 | 1.00** |

*The RRT-values may vary slightly due to variations in the mobile phase and due to column quality.
**The relative response of TM1 and impurity RRT 1.7 has not been determined.

Stability analysis was performed on crystalline particles after forced degradation at 40° C. and 75% relative humidity over 3 days. The results are shown in Table 4.

TABLE 4

| | Mo2S6O2 dimer (area %) | | | | | | |
|---|---|---|---|---|---|---|---|
| Time | A-2 | B-4 | B-1 | B-2 | B-3 | C-2 | C-1 |
| Initial | n.d | <0.05 | <0.05 | <0.05 | n.d | n.d | n.d |
| Day 1 | | 0.06 | 0.07 | 0.07 | <0.05 | | |
| Day 2 | | 0.23 | 0.14 | 0.13 | 0.07 | | |
| Day 3 | 0.09 | 0.38 | 0.2 | 0.19 | 0.11 | 0.03 | 0.02 |
| SSA (m²/g) | 0.26 | 1.16 | 0.60 | 0.65 | 0.38 | 0.08 | 0.23 |

| | TM2 (area %) | | | | | | |
|---|---|---|---|---|---|---|---|
| Time | A-2 | B-4 | B-1 | B-2 | B-3 | C-2 | C-1 |
| Initial | 0.29 | 0.01 | 0.01 | 0.01 | 0.01 | n.d. | 0.02 |
| Day 1 | | | | | | | |
| Day 2 | | | | | | | |
| Day 3 | 2.38 | 0.19 | 0.16 | 0.13 | 0.10 | 0.04 | 0.09 |

| | TM3 (area %) | | | | | | |
|---|---|---|---|---|---|---|---|
| Time | A-2 | B-4 | B-1 | B-2 | B-3 | C-2 | C-1 |
| Initial | 2.04 | 0.14 | 0.28 | 0.52 | 0.42 | 0.07 | 0.37 |
| Day 1 | | | | | | | |
| Day 2 | | | | | | | |
| Day 3 | 2.78 | 0.23 | 0.32 | 0.54 | 0.43 | 0.07 | 0.37 |

| | Total impurities (area %) | | | | | | |
|---|---|---|---|---|---|---|---|
| Time | A-2 | B-4 | B-1 | B-2 | B-3 | C-2 | C-1 |
| Initial | 2.34 | 0.20 | 0.32 | 0.56 | 0.44 | 0.11 | 0.39 |
| Day 1 | | | | | | | |
| Day 2 | | | | | | | |
| Day 3 | 5.54 | 1.01 | 0.81 | 0.97 | 0.68 | 0.14 | 0.51 |

Analysis was performed on 15 mg tablets made from crystalline particles of batches B-1 and C-1. The results are shown in Table 5.

TABLE 5

| | Batch | | |
|---|---|---|---|
| | B-1* | C-1** | C-2** |
| TM1 | 0.05% | <0.05% | <0.05% |
| TM2 | 0.31% | 0.1765 | 0.1% |
| TM3 | 0.77% | 0.4726 | 0.6% |
| Dimer $Mo_2S_6O_2^{2-}$ | 1.47% | 0.4255 | 0.4% |
| Dimer $Mo_2S_7O^{2-}$ | 0.1294% | <0.05% | 0.1% |
| RRT 1.76 | 0.0561% | <0.05% | <0.05% |
| Total Impurities | 2.78 | 1.074 | 1.26% |

Figure 8:
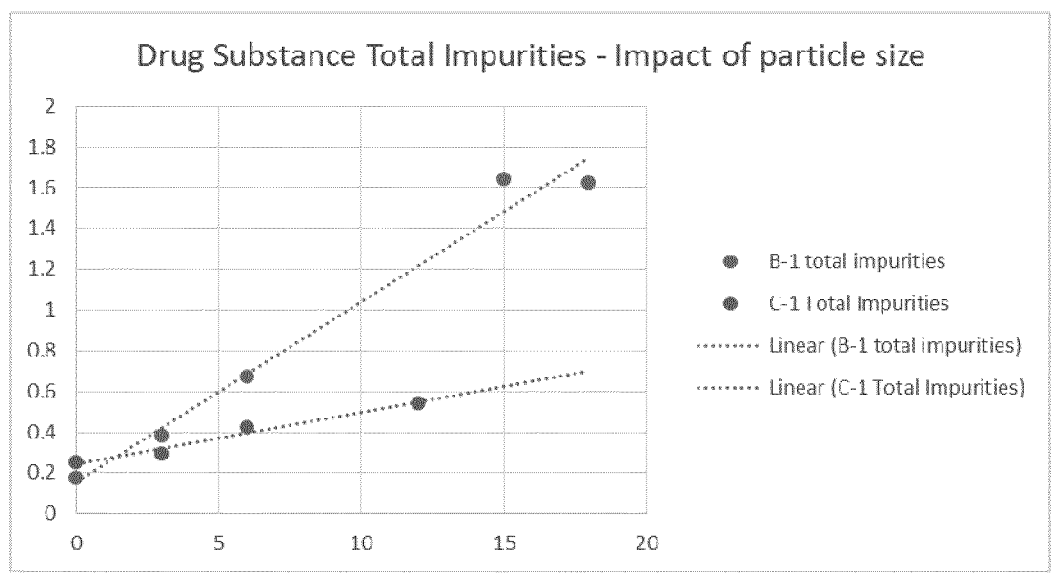
FIG. 8 shows a plot of total impurities over months storage at 2-8° C. controlled conditions, best linear fits are represented with dashed lines.

*Batch B-1 was stored for about 8 weeks at 2-8° C. prior to analysis
**Batches C-1 and C-2 were stored for about a week at 2-8° C. prior to analysis Example 8: Storage Stability Analysis The impact of the particle size for stability of bis-choline tetrathiomolybdate was exemplified by data from long term storage at 2-8° C. controlled conditions. The rate of degradation was significantly higher for lot B-1, with overall smaller particle size, than for lot C-1 with larger particles and manufactured by the disclosed process (FIG. 8; Table 6).

TABLE 6

| | | Month: | | | | | |
|---|---|---|---|---|---|---|---|
| | | 0 | 3 | 6 | 12 | 15 | 18 |
| B-1 | Tot. Imp. | 0.17 | 0.38 | 0.67 | | 1.64 | 1.62 |
| C-1 | Tot. Imp. | 0.25 | 0.29 | 0.42 | 0.54 | | |

Example 9: Impact of Process Variations

The crystallization conditions for Process C were further investigated to understand how variations in the temperature, ethanol charging time and stirring/mass transfer during crystallization impact isolated particle size, impurity levels, and yield of bis-choline tetrathiomolybdate (Table 7). In examples 1-7 and 9 of Table 7, 5 g crude WTX101 was dissolved in 17 mL purified water. Each mixture was then transferred to a 250 mL lab reactor via a series of 0.45 and 0.22 μm HPLC filters for polish filtration, and 2×1 mL water was used for rinsing (total amount water added: 19 mL, which gives an ethanol amount of 76 mL for an ethanol/water end-ratio of 80/20). After heating of the mixture to correct jacket temperature (35° C., 45° C., 50° C. or 55° C.), ethanol (76 mL) was charged for 1, 2.5 or 4 hours. A syringe pump connected to a 50-mL plastic syringe was used for the charging. Linear cooling profiles were then applied and all examples were cooled at a rate of 0.333° C./min down to 15° C. All mixtures were stirred for an additional 10 minutes at 15° C. before isolation of the solid on a P3 glass filter funnel. In example 8, the same conditions as described above were used, but the speed of the stirrer of the lab reactor was doubled. In example 10, the same conditions as described above were used, but a type different stirrer was used that increased the mass transfer in the lab reactor.

TABLE 7

| Ex. | Charge time (h) | Temp. (° C.) | $D_{10}$ (μm) | $D_{50}$ (μm) | $D_{90}$ (μm) | $D_{90}/D_{50}$ | <2 (%) | >100 (%) | TM3 (% w/w) | TM2 (% w/w) | Total impurities (% w/w) |
|---|---|---|---|---|---|---|---|---|---|---|---|
| 1 | 1 | 35 | 21 | 45 | 77 | 1.7 | 1.3 | 1.4 | 0.18 | <0.05 | 0.18 |
| 2 | 1 | 55 | 25 | 46 | 79 | 1.7 | 1.4 | 1.9 | 0.45 | 0.13 | 0.57 |
| 3 | 4 | 35 | 37 | 79 | 135 | 1.7 | 0.4 | 30 | 0.14 | <0.05 | 0.14 |
| 4 | 4 | 55 | 33 | 56 | 92 | 1.6 | 0.8 | 5.8 | 0.46 | 0.19 | 0.70 |
| 5 | 2.5 | 45 | 38 | 80 | 136 | 1.7 | 0.0 | 31 | 0.18 | <0.05 | 0.18 |
| 6 | 2.5 | 45 | 42 | 87 | 148 | 1.7 | 0.0 | 38 | 0.19 | <0.05 | 0.19 |
| 7 | 2.5 | 45 | 41 | 85 | 143 | 1.7 | 0.0 | 36 | 0.18 | <0.05 | 0.18 |
| 8 | 2.5 | 45 | 57 | 102 | 164 | 1.6 | 0.0 | 52 | 0.18 | <0.05 | 0.18 |
| 9 | 2.5 | 50 | 33 | 61 | 101 | 1.7 | 1.0 | 11 | 0.25 | 0.12 | 0.37 |
| 10 | 2.5 | 45 | 50 | 95 | 161 | 1.7 | 0.0 | 45 | 0.16 | <0.05% | 0.16 |

The isolated yields and assays were similar for all experiments and ranged from 89-94% and 99.4-100.0%, respectively.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed:

1. Crystalline particles of bis-choline tetrathiomolybdate (BC-TTM) having a $50^{th}$ percentile of particle size ($D_{50}$) of at least 30 μm.

2. The crystalline particles of claim 1 wherein the $D_{50}$ is at least 40 μm.

3. The crystalline particles of claim 2 wherein the $D_{50}$ is between 40 μm and 90 μm.

4. The crystalline particles of claim 1 having a $90^{th}$ percentile of particle size ($D_{90}$) of between 60 μm and 550 μm.

5. The crystalline particles of claim 4 wherein the $D_{90}$ is between 75 μm and 135 μm.

6. The crystalline particles of claim 5 wherein the $D_{90}$ is between 75 μm and 100 μm.

7. The crystalline particles of claim 1 having a specific surface area (SSA) less than 0.25 square meter per gram ($m^2/g$).

8. The crystalline particles of claim 1 wherein less than 40% percent of particles are greater than 100 μm.

9. A composition comprising the crystalline particles of claim 1 having less than 1 percent by mass of the bis-choline salt of $Mo_2S_6O_2^{2-}$.

10. A composition comprising the crystalline particles of claim 1 having less than 0.2 percent by mass of the bis-choline salt of $Mo_2S_7O^{2-}$.

11. The composition of claim 9 wherein percent by mass of $Mo_2S_6O_2^{2-}$ and/or the bis-choline salt of $Mo_2S_7O^{2-}$ is measured after storage at 40° C. and 75 percent relative humidity for three to six days.

12. A composition comprising the crystalline particles of claim 1 having less than 0.5 percent by mass of total impurities.

13. The crystalline particles of claim 12, wherein the total impurities comprise at least one of the bis-choline salts of TM1, TM2, TM3, $Mo_2S_6O_2^{2-}$, and $Mo_2S_7O^{2-}$.

14. The crystalline particles of claim 1 having a $D_{90}$-to-$D_{50}$ ratio less than 3.0.

15. The crystalline particles of claim 1, wherein the $D_{50}$ is less than 35 μm and/or $D_{90}$ is less than 75 μm.

16. A method for manufacture of the crystalline particles of bis-choline tetrathiomolybdate (BC-TTM) of claim 1, comprising:
   (a) providing a solution of BC-TTM in at least one solvent;
   (b) heating the solution of BM-TTM to a first temperature of between 35° C. and 50° C.;
   (c) gradually adding at least one of ethanol or isopropanol to the solution of BC-TTM over a time period of at least one hour, optionally at least two hours or two to four hours;
   (d) cooling the solution of BC-TTM to a second temperature of between 10° C. and 25° C. to produce BC-TTM crystalline particles;
   (e) filtering the BC-TTM crystalline particles;
   (f) drying the BC-TMM crystalline particles at a third temperature of between 20° C. and 30° C. under reduced pressure.

17. The method of claim 16, further comprising washing the BC-TTM crystalline particles with ethanol, optionally anhydrous ethanol, after filtering the BC-TTM crystalline particles and prior to drying the BC-TTM crystalline particles.

18. The method of claim 16, wherein the solution of BC-TTM is produced by dissolving solid BC-TTM that has previously been crystallized one or more times.

19. The method of claim 16, wherein the first temperature is between 40° C. and 45° C., the second temperature is 15° C., and/or the third temperature is 25° C.

20. A solid unit dosage form, comprising the crystalline particles of bis-choline tetrathiomolybdate of claim 1.

* * * * *